United States Patent [19]

Youngner et al.

[11] Patent Number: 4,842,855

[45] Date of Patent: Jun. 27, 1989

[54] ANTITUMOR PROCESS USING A *BRUCELLA ABORTUS* PREPARATION

[75] Inventors: Julius S. Youngner; David S. Feingold; Georg Keleti, all of Pittsburgh, Pa.

[73] Assignee: University of Pittsburgh, Pittsburgh, Pa.

[21] Appl. No.: 608,007

[22] Filed: May 7, 1984

Related U.S. Application Data

[63] Continuation of Ser. No. 218,076, Dec. 19, 1980, abandoned, which is a continuation of Ser. No. 49,880, Jun. 19, 1979, abandoned, which is a continuation-in-part of Ser. No. 889,273, Mar. 23, 1978, abandoned.

[51] Int. Cl.$^4$ ............................................. A61K 35/56
[52] U.S. Cl. ...................................................... 424/95
[58] Field of Search .......................................... 424/95

[56] References Cited

FOREIGN PATENT DOCUMENTS 17150 of 1971 Japan.

OTHER PUBLICATIONS

The Merck Index, 8th Ed., Merck and Co., Inc. Rahway, N.J. (1968), p. 313.

*Primary Examiner*—Jerome D. Goldberg
*Attorney, Agent, or Firm*—Arnold B. Silverman

[57] ABSTRACT

Preparing a nonviable, aqueous, ether-extracted *Brucella abortus* preparation (BRU-PEL) and introducing the same into a patient in a dosage effective to resist tumor development. The procedure may advantageously be followed either before the appearance of visible tumors or within a reasonable time after the appearance of the same.

11 Claims, No Drawings

ANTITUMOR PROCESS USING A *BRUCELLA ABORTUS* PREPARATION

CROSS-REFERENCE TO RELATED APPLICATION

This application is a continuation of U.S. Patent Application Ser. No. 218,076, which was filed on Dec. 19, 1980 (now abandoned), which in turn was a continuation of U.S. Patent Application, Ser. No. 49,880, which was filed on June 19, 1979 (now abandoned), which in turn was a continuation-in-part of U.S. Patent Application, Ser. No. 889,273, filed Mar. 23, 1978 (now abandoned).

BACKGROUND OF THE INVENTION

1. Field of the Invention

This invention relates to a process for inhibiting tumor development through the use of a *Brucella abortus* preparation, and, more specifically, relates to the use of a specific nonviable, aqueous, ether-extracted *Brucella abortus* preparation (BRU-PEL) which is introduced into the patient in a dosage effective to resist tumor development.

2. Description of the Prior Art

As a result of the great medical need to develop effective antitumor preparations, a large number of substances, both synthetic and of biological origin, have been investigated as immunomodulators in the treatment of tumors. Recently a great deal of work has centered around the use of living attenuated BCG (Bacillus Calmette-Guerin) organisms or killed cells of *Corynebacterium parvum* as biologically derived immunomodulators. With respect to the BCG organisms, there remains the risk of the patient's contracting tuberculosis as the organisms are live.

The beneficial use of *Brucella abortus* against tumors in mice has previously been known. See Z. Hirnle, "The Effect of Brucella Abortus Infection on Transmissible Crockers Sarcoma in Mice", *Acta Medica Polona*, pages 219–241 (1960), and Japanese Patent 17,150 (1971). This latter reference claims that a polysaccharide fraction obtained from heat-killed cells of *Brucella abortus* is capable of inhibiting growth of Sarcoma-180 in mice.

There remains a need for an improved antitumor agent which is less toxic, more stable and produces more uniform results than those previously known.

SUMMARY OF THE INVENTION

The above-described need has been met by the process of the present invention wherein a nonviable, aqueous, ether-extracted *Brucella abortus* preparation (BRU-PEL) is introduced into the patient in a dosage effective to resist tumor development. The material may be introduced into the patient either prior to detection of visible tumors or shortly thereafter.

It is a further object of the present invention to provide such a process wherein the material employed is less toxic and more stable, and the process produces more uniform results than materials previously employed.

It is a further object of this invention to provide a process which employs a nonviable, insoluble material which is stable in a powder form.

It is a further object of this invention to provide a process which may be employed with minimum risk of adverse effects on the patient while maximizing the antitumor effects of the process.

In addition, it is an object of the present invention to provide a process of tumor inhibition which may be employed in cooperation with the use of other anticancer drugs in combined modality therapy.

These and other objects of the invention will be more fully understood from the following description of the invention.

DESCRIPTION OF THE PREFERRED EMBODIMENTS

As used herein the expression "patient" refers to animals, including humans.

As used herein, the expressions "BRU-PEL" or "an ether-extracted *Brucella abortus* material" shall refer to either (1) a nonviable, ether-extracted *Brucella abortus* composition made by the process disclosed herein or (a) a nonviable *Brucella abortus* composition having generally the same composition and properties as the composition of category (1) set forth hereinabove in this paragraph.

The method of preparing BRU-PEL as well as its beneficial effects in interferon stimulation and antiviral properties have previously been disclosed. See Youngner, Keleti and Feingold, "Antiviral Activity of an Ether-Extracted Nonviable Preparation of *Brucella Abortus*", INFECTION AND IMMUNITY, December 1974, pages 1202–1206, and Feingold, Keleti and Youngner, "Antiviral Activities of *Brucella Abortus* Preparations: Separation of Active Components", INFECTION AND IMMUNITY, March 1976, pages 763–767.

BRU-PEL is a nonviable, partially lipopolysaccharide depleted derivative of Brucella abortus. It represents the insoluble residue which remains after living cells of *Brucella abortus* are extracted with aqueous ether.

We have found that BRU-PEL, when introduced into a patient, provides effective resistance to tumor development and particularly against cancerous tumor development. The introduction may be made prior to the appearance of visible tumors or thereafter.

The best method known to applicants of preparing BRU-PEL from *Brucella abortus* involves the following: a suitable *Brucella abortus* (strain 456) was obtained from the American Type Culture Collection, 12301 Parklawn Drive, Rockville, Md. 20852. The listing for the strain is "*Brucella abortus* Catalog No. 7705. Alice C. Evans, (NIH) 456. Preparation of Antigens (Medium 3, 37C)." The material was obtained from Dr. Evans. The *Brucella abortus* 456 strain which is a nonpathogenic strain used for antigen preparation, was grown in a tryptose broth with thiamine (Difco) supplemented with five percent calf serum (inactivated at 56° C. for 30 minutes). This strain of Brucella does not require addition of $CO_2$ for growth.

One liter of medium in a two-liter baffled Erlenmeyer flask was inoculated with about $5 \times 10^9$ viable Brucella and incubated at 37° C. for 48 hours with continuous shaking. The growing cells were harvested near the end of the log phase and viable counts were done in the usual manner on tryptose agar with thiamine and five percent inactivated calf serum.

The bacteria were harvested by centrifugation at 5,000 rpm ($4100 \times g$) for 35 minutes and washed once by suspension in cold, sterile, distilled water and recentrifugation. They were then suspended in cold water to give a Klett (Filter No. 66) reading of 470 to 500, which represented a viable count of $1 \times 10^{10}$ to $2 \times 10^{11}$ bacteria per milliliter. This and all subsequent operations were performed in sterilized equipment. Sterile, distilled water was used throughout.

The aqueous suspension was treated with diethyl ether by methods of Badakhsh and Foster, 1970, "Endotoxin-Containing Preparations of Brucella Abortus: Chemical Studies", *American Journal of Veterinary Research*, 31, 359–363, and Ribi, Haskins, Landy and Milner, 1961, "Preparation and Host Reactive Properties of Endotoxin with Low Content of Nitrogen and Lipid", *Journal of Experimental Medicine*, 114, 647–663. Two volumes of cold diethyl ether were added to one volume of cold aqueous suspension of Brucella, and the mixture was agitated for 10 minutes in a vibromixer and then allowed to stand at 25° C. overnight in a separatory funnel. The ether layer was discarded, and the aqueous phase containing the extracted bacteria was retained. Nitrogen was bubbled through the aqueous cell suspension until the odor of ether was undetectable. The extracted cells were removed by centrifugation, washed with distilled water and recovered by lyophilization of the aqueous heated suspension to yield BRU-PEL. BRU-PEL has the following gross composition (percentage by weight): protein 69%, total carbohydrate as glucose equivalents 10%, fatty acids 12%, and nucleic acid 4%. BRU-PEL generally has lipopolysaccharide content by weight of less than 1% and preferably less than 0.29%.

The aqueous material remaining after removal of the bacteria contained a significant amount of crude *Brucella lipopolysaccharide*.

In the experiments that are described hereinafter in connection with Tables 1–8, the mice employed were female Swiss Webster mice, weighing about 25 to 30 grams and were obtained from Taconic Farms of Germantown, N.Y. In general, either 10 or 15 mice were used in each experimental group.

In the experiments to be described below, wherein tumor cells of the Sarcoma-180 (S-180) type were employed, they were obtained in ascitic form from J. Molinari of the University of Pittsburgh.

Previous experiments have been performed by others in respect of the antitumor properties of *Brucella abortus*. In the Hirnle article identified above, it was reported that virulent living cells of *Brucella abortus* given intraperitoneally caused a thirty percent regression of tumors in mice given Sarcoma-180 cells subcutaneously in prolonged periods. It has also been reported that living cells of *Brucella abortus* given intraperitoneally prolonged the lives of mice infected with Rauscher leukemia virus. See Veskova, Chimishkyan and Svet-Moldavsky, 1974, "Effect of Brucella Abortus infection (Vaccine Strain 19BA) on Rauscher Leukemia Virus and L1210 Leukemia in Mice", *Journal of the National Cancer Institute*, 52, 1651–1653. In Pilet and Sabolovic, Bulletin of the French Association for Veterinary Microbiology and Immunology, Vol. 7, pages 43–57 (1970), it was reported that heat-killed and formalinized preparations of *Brucella abortus* injected intraperitoneally into mice afforded significant protection against Ehrlich ascites tumors. Heat-killed and formalinized preparation of *Brucella abortus* injected intraperitoneally into mice was also found to afford significant protection against the L1210 leukemia cells. See Le Garrec, Sabolovic, Toujas, Dazord, Guelfi and Pilet, BIO-MEDICINE 21: 40–43 (1974).

In the experiments described below, the S-180 cells in ascitic form were maintained by serial intraperitoneal passage in the mice every seven to ten days, the time required for grossly visible ascites to develop. Cells used in the experiments were recovered from ascitic fluid, washed once, resuspended in phosphate buffered saline (PBS) and counted in a hemocytometer. They were then diluted appropriately with PBS before intraperitoneal injection. The mice were observed daily for 50 days for abdominal swelling (ascites) or death. Statistical significance was determined by the student test t-criteria.

TABLE 1

Protection of mice against S-180 ascites tumor by BRU-PEL

| Treatment of mice at −1 day (0.2 ml ip)[a] | Protection of Mice | | | | | |
|---|---|---|---|---|---|---|
| | Ratio of ascites/ inoculated[b] | % | P | Ratio of dead/ inoculated[b] | % | P |
| PBS control | 15/15 | 100 | | 14/15 | 93 | |
| BRU-PEL, 2,000 ug | 0/15 | 0 | <0.001 | 0/15 | 0 | <0.001 |
| BRU-PEL, 500 ug | 5/15 | 33.3 | <0.001 | 3/15 | 20 | <0.001 |
| BRU-PEL, 125 ug | 3/15 | 20.0 | <0.001 | 2/15 | 13 | <0.001 |

[a]ip, Intraperitoneally Doses given one day before injection of S-180 ($10^4$ cells in 0.2 ml intraperitoneally at day 0).
[b]Observation period, 50 days In the test results tabulated in Table 1, all 15 mice which were injected with $10^4$ cells of S-180 developed ascites, and 14 died with the mean day of death of $23.6 \pm 4.7$. Table 1 shows that a single dose of BRU-PEL ranging from 2,000 to 125 micrograms given one day before injection of S-180 cells significantly inhibited ascites formation and death. The time of extraction of *Brucella abortus* with aqueous ether during the preparation of BRU-PEL had no effect on the antitumor activity as identical results were obtained with BRU-PEL prepared by ether water extraction with a vibromixer for 10, 20 or 30 minutes. BRU-PEL was relatively nontoxic with the mean lethal dose in the range of 7 to 15 milligrams per 25 grams of mouse body weight.

As is shown in Table 1, the 2,000 micrograms dose of BRU-PEL resulted in zero deaths in the inoculated mice and zero ascites formation. With reduced dosages, the results indicate that at 500 micrograms, a 20% fatality rate existed, and a 33.3% ascites formation ratio existed. At 125 micrograms, a 13.3% death rate existed, and a 20% ratio of formation of ascites.

As was shown in Table 1, a 2,000 microgram dose of BRU-PEL protected completely against $10^4$ cells of S-180 given one day later. This dose was used in a study of the time period during which BRU-PEL was effective.

TABLE 2

Protection of mice against S-180 ascites tumor: effect of time of injection BRU-PEL

| Tme of BRU-PEL treatment (2,000 ug ip)[a] | Protection of mice | | | |
|---|---|---|---|---|
| | Ratio of ascites/in- oculated[b] | % | Ratio of dead/inoc- ulated[b] | % |
| PBS control | 10/10 | 100 | 10/10[c] | 100 |
| −7 days | 3/9 | 33 | 3/9 | 33 |
| −4 days | 1/10 | 10 | 1/10 | 10 |
| −1 day | 2/10 | 20 | 1/10 | 10 |
| 0 day | 1/10 | 10 | 0/10 | 0 |

TABLE 2-continued

Protection of mice against S-180 ascites tumor: effect of time of injection BRU-PEL

| Tme of BRU-PEL treatment (2,000 ug ip)[a] | Protection of mice | | | |
|---|---|---|---|---|
| | Ratio of ascites/inoculated[b] | % | Ratio of dead/inoculated[b] | % |
| +1 day | 2/10 | 20 | 1/10 | 10 |
| +3 days | 2/10 | 20 | 2/10 | 20 |
| +7 days | 2/9 | 22 | 2/9 | 22 |

[a]Treatment in relation to injection of S-180 ($10^4$ cells intraperitoneally at day 0) ip, Intraperitoneally.
[b]Observation period, 50 days, −7 days, $P < 0.005$; −4 days to +7 days, $P < 0.001$.
[c]Mean day of death, $25.2 \pm 3.94$.

As is shown in Table 2, there is little difference in protection when BRU-PEL is given as early as seven days before or as late as seven days after injection of the tumor cells into the mice. BRU-PEL did not protect significantly when injected 14 days before or 10 days after challenge with S-180 cells.

Tests were performed to determine the influence of the number of S-180 cells injected as related to the protection offered by BRU-PEL. The results are shown in Table 3.

TABLE 3

Protection of mice against S-180 ascites tumor: effect of dose of tumor cells

| Treatment of mice at −1 day (0.2 ug ip)[a] | No. of S-180 cells (ip at day 0) | Protection of Mice | | | | | | |
|---|---|---|---|---|---|---|---|---|
| | | Ratio of ascites/inoculated[b] | % | P | Ratio of dead/inoculated[b] | % | P | Mean day of death |
| PBS control | $10^3$ | 8/10 | 80 | <0.001 | 8/10 | 80 | <0.001 | $29 \pm 4.8$ |
| BRU-PEL | | 0/10 | 0 | | 0/10 | 0 | | — |
| PBS control | $10^4$ | 10/10 | 100 | <0.05 | 10/10 | 100 | <0.01 | $20.3 \pm 3.1$ |
| BRU-PEL | | 4/8 | 50 | | 3/8 | 37.5 | | $36.7 \pm 2.5$[d] |
| PBS control | $10^5$ | 9/10 | 90 | <0.025 | 9/10 | 90 | <0.001 | $20.11 \pm 2.6$ |
| BRU-PEL | | 4/9 | 44.4 | | 1/9 | 11.1 | | — |
| PBS control | $10^6$ | 15/15 | 100 | <0.001 | 15/15 | 100 | <0.001 | $17.7 \pm 2.1$ |
| BRU-PEL | | 6/15 | 40 | | 4/15 | 26.6 | | $33 \pm 5.1$[d] |
| PBS control | $10^7$ | 15/15 | 100 | NS[e] | 15/15 | 100 | NS[e] | $16.3 \pm 2.0$ |
| BRU-PEL | | 15/15 | 100 | | 15/15 | 100 | | $20.27 \pm 1.0$[d] |

[a]2,000 ug amount of BRU-PEL was given intraperitoneally (ip) in 0.2 ml.
[b]Observation period, 50 days.
[c]Dashes indicate insufficient sample to permit calculation.
[d]$P < 0.001$.
[e]NS, Not significant.

It is noted that an inoculum of as few as $10^3$ cells of S-180 killed 80% of the control mice within 50 days, with the mean day of death being $29 \pm 4.8$. With increased doses of tumor cells, the mean day of death decreased. A single BRU-PEL injection of 2,000 micrograms given one day before challenge with doses of S-180 cells ranging from $10^3$ to $10^7$ significantly prolonged survival times of the mice. When $10^7$ S-180 cells were used as the challenge, ascites and death were not prevented by a single dose of BRU-PEL; however, the survival time was increased by 25% (P less than 0.001).

As has been mentioned in the foregoing, one of the materials receiving great attention in respect of antitumor properties is *Corynebacterium parvum* (*C. parvum*). Tests were performed in order to obtain a comparison between the performance of *C. parvum* and BRU-PEL. The results of these tests are shown in Table 4.

TABLE 4

Protection of mice against S-180 ascites tumor by BRU-PEL and by *C. parvum* preparations

| Treatment of mice at −1 day[a] | Protection of Mice | | | | | | |
|---|---|---|---|---|---|---|---|
| | Ratio of ascites/inoculated[b] | % | P | Ratio of dead/inoculated[b] | % | P | Mean day of death | P |
| PBS control | 10/10 | 100 | | 10/10 | 100 | | $21.90 \pm 2.90$ | |
| BRU-PEL (1,000 ug | 4/8 | 50 | <0.02 | 3/8 | 38 | <0.01 | $33.33 \pm 14.01$ | <0.05 |
| *C. parvum* 1,000 ug in 0.2 ml, ip) | 9/10 | 90 | NS[d] | 9/10 | 90 | NS[d] | $24.78 \pm 4.00$ | NS[d] |

[a]Before injection of S-180 ($10^4$ cells in 0.2 ml intraperitoneally at day 0).
[b]Observation period, 50 days.
[c]Intraperitoneally
[d]NS, Not significant The three categories reported in Table 4 are the PBS control, the BRU-PEL and the *C. parvum*. It is noted that when identical doses of 1,000 micrograms of BRU-PEL and *C. parvum* were given to mice one day before challenge with $10^4$ S-180 cells, only BRU-PEL protected effectively against ascites and death. The rate of ascites for BRU-PEL was only 50% as contrasted with 90% for *C. parvum*, and the rate of death was only 38% for BRU-PEL as contrasted with 90% for *C. parvum*. The *C. parvum* preparation failed to delay significantly the mean day of death. Similar results were obtained by using 2,000 micrograms of either BRU-PEL or *C. parvum* (15 mice per group).

An effort was made to determine the effect of multiple doses of BRU-PEL. The results of these tests are set forth in Table 5.

TABLE 5

Protection of mice against
S-180 ascites tumor by repeated doses of BRU-PEL

| Treatment of mice | Day of Treatment[a] | Protection of mice | | | | | |
|---|---|---|---|---|---|---|---|
| | | Ratio of ascites/inoculated[b] | % | P | Ratio of dead/inoculated[b] | % | P |
| PBS control | −1 | 10/14 | 71.4 | | 10/14[c] | 71.4 | |
| BRU-PEL (500 ug ip) | −1 | 0/15 | 0.0 | <0.001 | 0/15 | 0.0 | <0.001 |
| BRU-PEL (500 ug ip) | −1, +1, +3 | 0/15 | 0.0 | <0.001 | 0/15 | 0.0 | <0.001 |
| BRU-PEL (100 ug ip) | −1 | 5/13 | 38.5 | NS[d] | 5/13 | 38.5 | NS |
| BRU-PEL (100 ug ip) | −1, +1, +3 | 3/15 | 20.5 | <0.01 | 3/15 | 20.0 | <0.01 |

[a]In relation to injection of S-180 ($10^4$ cells intraperitoneally (ip) at day 0).
[b]Observation period, 50 days.
[c]Mean day of death, 24.4 ± 2.49.
[d]NS, Not significant.

A single intraperitonal dose of 500 micrograms of BRU-PEL given one day before $10^4$ cells of S-180 prevented ascites and death in all 15 mice tested. As can be seen from Table 5, identical results were obtained when the mice were given additional injections of 500 micrograms of BRU-PEL one and three days after the tumor cells were injected. A single intraperitoneal dose of 100 micrograms of BRU-PEL given one day before the tumor cells did not significantly prevent ascites formation or death. However, when the mice were given two additional injections of 100 micrograms of BRU-PEL one and three days after the tumor cells, there was significant protection against development of ascites (P less than 0.01) and death (P less than 0.01).

Tests were performed to determine whether BRU-PEL administered asynchronously with cyclophosphamide resulted in greater inhibition of transplanted mammary tumors in C3H mice than that observed for either agent alone. Similar tests were performed with *C. parvum*.

The following methods were employed: The tumor used was a mammary carcinoma which arose in C3H mice and was transferred in C3HeB mice; $2 \times 10^5$ viable tumor cells were inoculated subcutaneously into the left hind leg distal to the popliteal mode of 8 to 12 week old mice. Treatment regimens were begun when tumors were about 5 mm in diameter (14 days following injection). Cyclophosphamide (60 mg/kg) was given i.p. every seven days. BRU-PEL (1.4 mg/mouse) or *C. parvum* (1.4 mg/mouse) was injected i.p., i.v., or into the tumor (i.t.) every seven days (4 days after each cyclophosphamide injection). Control mice received diluent instead of cyclophosphamide or the bacterial preparations. Tumor diameters were measured at weekly intervals.

BRU-PEL alone either i.p. or i.t. had no effect on tumor growth; in this respect BRU-PEL behaved similarly to *C. parvum*. However, a significant inhibition of tumor growth was seen when BRU-PEL was given i.t. in combination with cyclophosphamide (CY). Combined therapy with BRU-PEL i.t. and CY i.p. resulted in total regression of 50% of the tumors.

In addition, BRU-PEL given by different routes in combination with cyclophosphamide markedly prolonged the survival of tumor-bearing mice. At 56 days after initiation of one experiment, the percentage of survivors in the different groups were as follows: CY alone, 17%; BRU-PEL, i.p.+CY, 67%; BRU-PEL, i.v.+CY, 50%; BRU-PEL i.t.+CY, 75%.

In another experiment, tests were conducted to compare the effects of BRU-PEL and *C. parvum* given by different routes, with or without cyclophosphamide. The results in Table 6 demonstrate that in combination with cyclophosphamide, BRU-PEL produces striking antitumor effects. When considering the number of mice surviving, survival time, and complete regression of tumors, the antitumor activity of BRU-PEL was as good as, if not better than, that of *C. parvum*.

TABLE 6

Comparison of antitumor effects of
*C. parvum* and BRU-PEL given by
different routes, with and without Cyclophosphamide (CY)

| Group | Treatment | Median survival time (days) | Range | Number of Mice | Survivors (56 days) | Complete Regression |
|---|---|---|---|---|---|---|
| I | Saline | 25 | 18–46 | 12 | 0 | 0 |
| II | Cyclophosphamide (CY) | 56 | 46–56+ | 12 | 5 | 0 |
| III | *C. parvum* i.p. | 28 | 21–35 | 12 | 0 | 0 |
| IV | *C. parvum* i.p. + CY | 56+ | 35–56+ | 12 | 10 | 2 |
| V | BRU-PEL i.p. | 27 | 18–35 | 12 | 0 | 0 |
| VI | BRU-PEL i.p. + CY | 56+ | 28–56+ | 12 | 8 | 0 |
| VII | BRU-PEL i.t. | 28 | 4–46 | 12 | 0 | 0 |
| VIII | BRU-PEL i.t. + CY | 56+ | 46–56+ | 12 | 11 | 6 |

The effect of bone marrow macrophage colony production in normal and tumor-bearing mice was examined. A single injection of BRU-PEL (1.4 mg/mouse) was given intraperitoneally (i.p.) to normal C3HeB mice or to mice bearing mammary tumors in the left hind leg. Bone marrow macrophage colony formation was assayed using the method of Baum and Fisher, Cancer Research 32, 2813–2817 (1972), expressed as a percent of colony production compared to bone marrow from saline controls (100%). BRU-PEL produced a marked stimulation of macrophage colony production in normal mice at one day (370%), in three days (785%). In tumor-bearing mice, BRU-PEL produced an early enhancement of colony production (270%, three days after injection). Although no direct comparison with *C.*

*parvum* was carried out in these experiments, comparison of BRU-PEL results with published data on *C. parvum* suggests that BRU-PEL may be at least as active a stimulator of macrophage activity as *C. parvum*.

In order to study adjuvant effect of various materials on the protective effect produced by tumor cells vaccines, a test was performed. X-irradiated, L1210 cell vaccine ($1 \times 10^7$ cells i.p.) alone did not protect MBL-2 mice against an i.p. challenge seven days later with $1 \times 10^4$ viable L1210 tumor cells. Various adjuvant materials given to mice on the same day as vaccine potentiated immunizing action of the inactivated tumor cell vaccine. A standard by which the new adjuvant materials were evaluated was pyran copolymer. Preliminary tests with BRU-PEL in the experimental model revealed that the BRU-PEL on a body weight-to-dose basis was a more active adjuvant than pyran copolymer. Doses of BRU-PEL as low as one mg/kg provided the equivalent adjuvant action in the L1210 vaccine system as 5 to 20 mg/kg of pyran copolymer. Groups of mice received $1 \times 10^7$ irradiated L1210 cells i.p. on day $-7$ together with various doses of BRU-PEL either i.p. or i.v. On day zero (7 days after vaccination), the mice were challenged i.p. with $1 \times 10^4$ viable L1210 cells, and deaths were recorded daily for 60 days. At the end of this observation period, all survivors were challenged i.p. with $1 \times 10^4$ L1210 cells, and deaths were recorded for another 30 days. The data in Table 7 show that BRU-PEL is an active adjuvant in the L1210 cell vaccine system. As little as 0.8 mg/kg i.p. of BRU-PEL potentiated the vaccine protection against challenge. Vaccine alone protected only 1/34 mice (MST=16 days) whereas 0.8 mg/kg of BRU-PEL augmented the vaccine effect and protected 15/20 mice (MST=greater than 60 days). In addition, surviving mice were almost uniformly resistant to second challenge with viable L1210 cells 60 days after the first challenge doses indicating the production of a state of solid immunity. BRU-PEL given i.v. was not as effective as by i.p. route when used as an adjuvant. This lower adjuvant potency by the i.v. route was also noted with pyran copolymer, which failed to add to the protective effect of L1210 vaccine when given i.v. The inability of a large dose of BRU-PEL (16 mg/kg) as an adjuvant is not understood. In general, drugs which exhibit an adjuvant effect in the L1210 vaccine system also prove effective when used as immunostimulators when combined with modality treatment.

TABLE 7

Potentiation of L1210 Vaccine by BRU-PEL and Resistance to Subsequent Challenge

| | Vaccine ($1 \times 10^7$)[a] | BRU-PEL[b] Day 7 mg/kg | route | L1210 ($1 \times 10^4$) i.p. | Results[c] Mean survival time (days) | S/T | Rechallenge S/T[d] |
|---|---|---|---|---|---|---|---|
| 1 | D-7 | — | — | — | | 33/33 | 1/33 |
| 2 | D-7 | — | — | Day 0 | 11 | 1/34 | 1/1 |
| 3 | D-7 | 0.4 | i.p. | Day 0 | 16 | 3/20 | 2/3 |
| 4 | D-7 | 0.8 | i.p. | Day 0 | >60 | 15/20 | 14/15 |
| 5 | D-7 | 0.6 | i.p. | Day 0 | >60 | 17/20 | 17/17 |
| 6 | D-7 | 3.2 | i.p. | Day 0 | >60 | 16/22 | 16/16 |
| 7 | D-7 | 4.0 | i.p. | Day 0 | >60 | 13/21 | 13/13 |
| 8 | D-7 | 8.0 | i.p. | Day 0 | >60 | 11/22 | 11/11 |
| 9 | D-7 | 16.0 | i.p. | Day 0 | 12 | 1/21 | 1/1 |
| 10 | D-7 | 0.8 | i.v. | Day 0 | 12 | 0/20 | |
| 11 | D-7 | 3.2 | i.v. | Day 0 | 18 | 2/20 | 2/2 |
| 12 | D-7 | 4.0 | i.v. | Day 0 | 20 | 5/20 | 4/5 |
| 13 | D-7 | — | — | Day 0 | 10 | 0/20 | |
| 14 | D-7 | — | — | — | 60 | 20/20 | 0/20 |

[a]Indicated groups received $1 \times 10^7$ radiated vaccine cells i.p. on day $-7$.
[b]Animals received BRU-PEL on day $-7$ by route indicated.
[c]Animals scored for survival 60 days following L1210 challenge on day 0.
[d]S/T, survivors/total, scored at 90 days after rechallenge with $1 \times 10^4$ L1210 cells on day 60.

Nonspecific macrophage activation collates well with the capacity to enhance host resistance against neoplasia. The ability of BRU-PEL to activate macrophages in vivo was tested by the method of Schultz, Papametheakis and Chrigos, *Cellular Immunology*, 29, 403–409 (1977). Peritoneal macrophages for male CD$_2$Fl mice were obtained six days after i.p. administration of various doses of BRU-PEL or pyran copolymer. Approximately $1 \times 10^6$ macrophages (purified by adherence) were tested for their ability to inhibit the growth in culture of an established line of murine leukemia cells (MBL-2). The percentage of growth inhibition of MBL-2 cells to the effect of BRU-PEL or pyran copolymer was calculated by comparison with MBL-2 cells, grown in the presence of macrophages from mice not stimulated with BRU-PEL or pyran copolymer. The data in Table 8 shows that macrophages from mice given BRU-PEL or pyran copolymer (10 mg/kg) produce significant inhibition of growth of MBL-2 target cells; a lower dose of BRU-PEL (1 mg/kg) was without effect. These results again emphasize that BRU-PEL is a potent nonspecific activator of macrophage activity in vivo.

TABLE 8

Comparison of nonspecific macrophage activation in vivo by BRU-PEL and pyran copolymer. Inhibition of growth of the MBL-2 line of mouse leukemia cells in culture

| Macrophages[a] from mice given | Dose (mg/kg, i.p.) | % Growth Inhibition[b] |
|---|---|---|
| PBS | 0.2 ml | 0 |
| Pyran copolymer | 10 | 94 |
| BRU-PEL | 1 | 4 |
| | 10 | 98 |
| | 100 | 91 |

[a]Peritoneal macrophages obtained 6 days after i.p. administration of drug or control.
[b]Target cells, MBL-2 leukemia cells in culture according to method of Schultz et al (Cell Immunology, 29–55) (1977).

In another test, one thousand mg of BRU-PEL were given i.p. to six-week old C57B1/6 mice. Fourteen days later experimental control animals were challenged with an LD$_{100}$ of *Listeria monocytogenes*. Mortality was 10/10 among control, and 0/10 in BRU-PEL treated animals. Peritoneal macrophages harvested 3, 7 and 10 and 14 days after BRU-PEL administration were cytotoxic for murine osteogenic sarcoma cells in vitro. Macrophages from BRU-PEL treated mice showed enhanced chemiluminescence over those control mice during phagocytosis with zymosan. These data strongly suggest that BRU-PEL shares a number of properties with other immunomodulators, such as *C. parvum* and represents a new therapeutic agent characterized by the capacity to induce interferon, activate the RES nonspecifically, enhance host resistance to virus infection and protect animals against tumor transplants.

In an effort to determine the influence of the route of administration of BRU-PEL, intravenous injections were made. Intravenous injection of BRU-PEL (2,000 micrograms) into mice one day before the tumor cell challenge did not prevent ascites or death. However, the mean day of death was delayed significantly, 20.3±3.09 for untreated controls and 27.5±9.23 for treated animals (P less than 0.01).

The results of these tests show that BRU-PEL protects outbred mice against S-180 ascites tumors. The extent of protection is a function of the relative doses of BRU-PEL and tumor cells, as well as the time of injection of BRU-PEL. Under optimal conditions (2,000 micrograms of BRU-PEL intraperitoneally one day before $10^3$ cells of S-180), no ascites developed and all animals survived. When an inoculum of $10^7$ tumor cells was employed, there was a significant (P less than 0.001) delay in the time of death of treated mice, although death eventually occurred. BRU-PEL protected mice even when given as early as seven days before or as late as seven days after the challenge by S-180 cells. A single dose of BRU-PEL did not significantly affect the course of the tumor if given after the appearance of obvious ascites. However, preliminary results suggest that a multidose schedule of BRU-PEL may cause regression of established ascites tumors.

Murine Osteogenic Sarcoma Tests

Experiments were performed to determine the capacity of BRU-PEL to enhance host resistance to the development of a transplantable osteogenic sarcoma in mice.

C57B1/6J female mice obtained from Jackson Laboratories, Bar Harbor, Maine were used in these experiments. The mice were six to ten weeks of age and were given food and water ad libitum.

BRU-PEL in lyophilized powder form was suspended in phosphate buffered saline (PBS) to a concentration of 10 mg/ml. Each mouse received 1000 ug of BRU-PEL intraperitoneally (i.p.) in 0.1 ml. *C. parvum* was provided as a killed vaccine containing 7 mg/ml wet weight of organisms. Mice were inoculated i.p. with 1400 ug per mouse. The polyinosinic-polycytidylic acid-poly-L-lysine complex [poly (1CLC)] was prepared and furnished by H. B. Levy, National Institutes of Allergy and Infectious Disease. Each mouse was given 100 ug i.p. in 0.1 ml.

A continuous line of osteogenic sarcoma (OGS) cells that has remained tumorigenic upon ip or subcutaneous (S.C.) inoculation into C57B1/6J mice was established from a primary osteogenic sarcoma of the vertebrae induced in C57B1/6J mice by irradiation with 239 Plutonium (provided by G. Taylor, Division of Radiobiology, University of Utah). Histologic sections of the primary tumor demonstrated the characteristics of an osteogenic sarcoma. The osteoid component was lost with in vitro or in vivo passage and S. C. inoculation of the OGS cell line produced an undifferentiated sarcoma. All cell cultures were propagated and maintained on Eagle's minimal essential medium (MEM) containing 10% fetal bovine serum, 300 ug of glutamine per ml, 100 U penicillin per ml, and 50 ug of streptomycin per ml. Cells were incubated in humidified 5% $CO_2$ atmosphere at 37 C.

In an initial experiment to determine whether animals could be protected against the development of transplanted osteogenic sarcomas by administration of BRU-PEL, groups of ten C57B1/6J mice were inoculated ip with $1 \times 10^5$ OGS cells. In preliminary experiments tumors developed within the peritoneal cavity and death occurred over a two-to-three-month period. BRU-PEL or *C. parvum* was administered either 14 days prior to (−14 d) or immediately preceding (0 d) tumor inoculation. The results of this experiment are summarized in Table 9.

TABLE 9

Capacity of BRU-PEL and *C. parvum* to enhance resistance of C57B1/6J mice to transplanted osteogenic sarcomas

| Treatment | | Mortality Number | % |
|---|---|---|---|
| Experiment 1 | | | |
| PBS | | 10/10 | 100 |
| BRU-PEL | −14 days | 1/10 | 10[a] |
| BRU-PEL | 0 day | 0/10 | 0[a] |
| C. parvum | −14 days | 3/8 | 37[c] |
| C. parvum | 0 days | 0/9 | 0[a] |
| Experiment 2 | | | |
| PBS | | 19/20 | 95 |
| BRU-PEL | −14 days | 10/20 | 50[b] |
| BRU-PEL | 0 day | 7/17 | 41[a] |
| BRU-PEL | +3 days | 6/18 | 33[a] |
| BRU-PEL | +7 days | 13/18 | 72 |
| C. parvum | −14 days | 12/20 | 60[c] |
| C. parvum | 0 day | 7/15 | 47[b] |
| NDV | −14 days | 20/20 | 100 |
| NDV | 0 day | 18/18 | 100 |
| poly (ICLC) | −14 days | 18/18 | 100 |
| poly (ICLC) | 0 day | 12/16 | 75 |

[a] $p < 0.001$
[b] $p < 0.01$
[c] $p < 0.05$ (Experiment 1). After three months all the control animals treated with PBS had died while only one death occurred among the mice treated with BRU-PEL and three from the group that received *C. parvum*. In all surviving animals, tumor development was completely inhibited during the observation period. These data suggested that BRU-PEL was effective in enhancing host resistance to the development of tumors after inoculation of OGS cells.

In the next experiment the treatment schedule was expanded to determine how late in the course of tumor development host resistance could be enhanced. Results reported previously from our laboratory that the growth of OGS cells is inhibited by interferon in vitro and in vivo and the fact that BRU-PEL induces interferon in mice suggested that interferon might be a factor in the observed efficacy of BRU-PEL in suppressing tumor development. Newcastle disease virus (NDV) was obtained from S. Baron (NIH, Bethesda, Md.). The pool used in these studies was prepared in embryonated chicken eggs and titered $4 \times 10^8$ PFU/ml in fetal lamb kidney (FLK) cells. In order to control for this variable, groups of animals also received either NDV or poly (ICLC) at 14 days before or just prior to OGS cells. The poly (ICLC) was utilized as a synthetic interferon inducer which stimulates high levels of interferon in mice. One group of animals was inoculated with each interferon inducer 14 days before the tumor cells in order to control for the possibility that these inducers might also act as a nonspecific modulator of host resistance. The results are also summarized in Table 1 (Experiment 2). After two months of observation, the mortality of tumor-inoculated mice was significantly reduced when BRU-PEL was administered at either −14 d, 0 d, or 3 d after, but not at 7 d after tumor cells. C. parvum was also effective when given 14 d before or on 0 d while the interferon inducers, NDV and poly (ICLC) failed to offer any protection against the development of tumors.

The next series of experiments were designed to attempt to delineate the mechanism of action of BRU-PEL. In our laboratory, a number of immunomodulators including BRU-PEL have been shown to protect animals against viral infections in addition to enhancing resistance to tumor development. The timing of effective administration suggested that both antiviral and antitumor activity was the result of nonspecific immunomodulation of host defenses. Activation of macrophages has been postulated as one common mechanism of action of the diverse activities of immunomodulators. The capacity of immunomodulators to activate macrophages is evidenced by enhanced phagocytic capacity, the ability to be cytocidal for tumor cells, and to limit the progress of a viral infection in monolayers of susceptible cells in vitro.

Peritoneal Cells (PC) were harvested from experimental and control mice 14 days after BRU-PEL, C. parvum or poly (ICLC) administration as described previously. Briefly, mice were sacrificed by cervical dislocation and the peritoneum exposed. The peritoneal cavities were irrigated with 5-6 ml of cold MEM without serum and containing 2.5 units/ml of sodium heparin. The peritoneal washings were collected and pooled from animals of the same group. Fluids containing PC were then centrifuged at 350×g. For demostration of in vitro antitumor, PC were resuspended in MEM with 10% serum. Viable PC were then counted using trypan blue (0.006%) exclusion.

To determine whether BRU-PEL treatment could enhance the tumoricidal capacity of macrophages, PC were harvested from animals inoculated with BRU-PEL or control preparations. PC were suspended at various concentrations in MEM and 0.2 ml of each PC suspension was added to each well of 96 well micro titer plates (Linbro, Flow Labs, Inglewood, California) and allowed to attach for two hours at 37° C. Cell concentrations were adjusted to provide PC: target cell ratios of 40:1, 20:1, 10:1, and 5:1. Non-adherent cells were removed by two PBS washer and 0.2 ml of medium containing either OGS or MEF target cells was added. Duplicate or triplicate wells of each PC concentration alone and target cells alone served as controls. After 72 hours incubation, supernatant medium was removed and the cells were fixed and stained with methylene blue. The monolayers were examined microscopically and compared with controls to determine antitumor activity as evidenced by a cytotoxic effect. Cytotoxicity was scored by estimating the percentage of cellular destruction when compared with the respective control wells. The results of one of five similar experiments are presented in Table 10.

TABLE 10

The cytotoxicity of adherent peritoneal cells from BRU-PEL-treated mice for osteogenic sarcoma cells and syngeneic mouse embryo fibroblasts.

| Target Cell | Monolayer Confluency Expressed as % Peritoneal cell: Target cell ratio | | | | | | | | |
|---|---|---|---|---|---|---|---|---|---|
| | BRU-PEL-Treated Mice | | | | | Control Mice | | | |
| | Control | 40:1 | 20:1 | 10:1 | 5:1 | 40:1 | 20:1 | 10:1 | 5:1 |
| OGS | 100% | <10% | 25% | 60% | 100% | 100% | 100% | 100% | 100% |
| MEF | 100% | <10% | 30% | 65% | 100% | 100% | 100% | 100% | 100% |

Each average value is the percent of the monolayer remaining intact after exposure to activated or control PC. In these experiments the cytotoxic effect of a particular set of PC was evaluated as positive if the average percent confluency was less than 50% with PC: target cell ratios of 20:1 or less. In other experiments, PC were harvested from animals exposed to C. parvum, a recognized immunomodulator and poly (ICLC). In all experiments, C. parvum activated peritoneal macrophages to be cytocidal for OGS cells while PC obtained from animals inoculated with poly (ICLC) or from control animals failed to affect either OGS or MEF cells. It should also be noted that in these experiments we consistently observed that activated macrophages also were cytocidal for syngeneic MEF.

Osteogenic sarcoma is probably the most common malignant primary tumor of bone in humans and although the prognosis of patients with this malignancy has improved, therapy remains far from optimal. The results of these tests support the efficacy of BRU-PEL in preventing the development of tumors in experimental animals after administration of 100% lethal inoculum of osteogenic sarcoma cells. This effect was observed not only with pretreatment, but also when BRU-PEL was administered after tumor cells were inoculated.

Murine Leukemia Tests

Tests were performed to determine whether BRU-PEL when used as an adjuvant to chemotherapy would produce a beneficial effect in the treatment of a murine leukemia.

A Moloney lymphoid leukemia line, LSTRA, originally induced in BALB/c ($H-2^d$) mice by the Moloney murine leukemia virus, has been maintained and routinely passaged in our laboratory as a transplantable tumor line for several generations in (BALB/c×-DBA/2)$F_1$ ($H-2^d$) (CD2$F_1$) mice. The ascitic tumor is serially transplanted ip at weekly intervals.

The M109 ($H-2^d$) (BALB/c) murine alveolar carcinoma tumor cell line has been maintained and routinely passaged in our laboratory as a transplantable tumor line for greater than 40 generations in BALB/c male mice. The tumor is serially transplanted sc at intervals of 3 weeks.

The L1210 ($H-2^d$) (DBA/2) murine leukemia tumor cell line was maintained and routinely passaged in DBA male mice at weekly intervals by the ip route.

Adult CD2F$_1$ male mice, 6–8 weeks old, were obtained from the National Cancer Institute, Bethesda, Md. The animals were housed in plastic cages and fed Purina laboratory chow with water ad libitum.

BCNU was supplied by the National Cancer Institute. The alkylating agent was dissolved in a steroid-suspending vehicle and administered sc in a constant volume of 0.01 ml/g of body weight. Levamisole was supplied by Dr. P. Janssen, Janssen Pharmaceutica, Beerse, Belgium. The chemical was dissolved in sterile 0.85% NaCl solution and administered ip in a constant volume of 0.01 ml/g of body weight. The aqueous ether-extracted residue was dissolved in sterile 0.85% NaCL solution and administered ip in a constant volume of 0.01 ml/g of body weight.

The response of LSTRA leukemia to chemotherapy and BRU-PEL adjuvant treatment is shown in Table 11. BCNU therapy was withheld until systemic leukemia was established (Day 7 after tumor inoculation). BCNU therapy alone was effective in prolonging the median survival time (MST) by 3 weeks over the control non-treated group, with 30% of the animals alive and tumor-free at 90 days when the experiments were terminated. The additional treatment with BRU-PEL during the early drug-induced remission period (Day 12), 5 days after BCNU treatment, resulted in a more extended survival period and a larger number of tumor-free survivors. Multiple treatment with BRU-PEL did not appear to be any more beneficial than single treatment.

Three groups of mice were treated with BRU-PEL alone, by different routes, as comparative control groups to untreated and BCNU-treated mice to assess whether BRU-PEL exerted a tumor-retarding effect. BRU-PEL, when administered alone by the ip, iv, or intratumoral route, resulted in an increase of 41%, 25% or 8% respectively.

TABLE 11

Response of LSTRA leukemia to BRU-PEL adjuvant

| BCNU* (30 mg/kg) | BU-PEL mg/kg | Day | Route | Survivors (%) | MST (days) |
|---|---|---|---|---|---|
|  |  |  |  | 0 | 12 |
| + |  |  |  | 30 | 33 |
| + | 4 | 12 | ip | 90 | >90 |
| + | 8 | 12 |  | 80 | >90 |
| + | 16 | 12 |  | 100 | >90 |
| + | 8 | 12, 19, 26 |  | 60 | >90 |
| + | 4 | 12 | iv | 80 | >90 |
| + | 8 | 12 |  | 60 | >90 |
| + | 16 | 12 |  | 100 | >90 |
| + | 8 | 12, 19, 26 |  | 60 | >90 |
| + | 4 | 12 | Intratumoral | 30 | 41 |
| + | 8 | 12 |  | 50 | 90 |
| + | 16 | 12 |  | 50 | 90 |
|  | 16 | 12 | ip | 0 | 17 |
|  | 16 | 12 | iv | 0 | 15 |
|  | 16 | 12 | Intratumoral | 0 | 13 |

*Treatment 7 days after sc inoculation of $10^5$ LSTRA cells.

The significant increases attained in both survival period (MST) and percentage of survivors demonstrate the synergistic effect exerted by combined BCNU and BRU-PEL adjuvant treatment. Intratumoral injection of BRU-PEL did not appear to be as effective as the ip or iv route in increasing the percentage of survivors. The 16-mg/kg dose of BRU-PEL appears to be the most effective dose of the three doses tested.

Table 12 contains the results of a study comparing the adjuvant effect of BRU-PEL and levamisole, an agent previously reported to possess immunostimulatory effect. Similar, effective response rates were achieved with both BRU-PEL and levamisole adjuvants when they were administered by the ip or iv route. No statistical differences were noted for the two doses tested of each adjuvant when administered by these two routes. Levamisole was more effective than BRU-PEL when the sc route was employed. Although levamisole was effective when given orally, BRU-PEL did not exhibit any adjuvant effect when given by this route. The responses attained by levamisole and BRU-PEL when these agents were used in conjunction with chemotherapy show that both agents possess immunoadjuvant activity.

TABLE 12

Response of LSTRA leukemia to chemotherapy and levamisole and BRU-PEL adjuvant

| BCNU* (30 mg/kg) | Adjuvant (mg/kg)+ Levamisole | BRU-PEL | Route | Survival (%) | MST (days) |
|---|---|---|---|---|---|
|  |  |  |  | 0 | 12 |
| + |  |  |  | 30 | 32 |
| + | 5 |  | ip | 80 | >100 |
| + | 20 |  |  | 70 | >100 |
| + |  | 4 |  | 90 | >100 |
| + |  | 16 |  | 100 | >100 |
| + | 5 |  | sc | 90 | >100 |
| + | 20 |  |  | 70 | <100 |
| + |  | 4 |  | 30 | 42 |
| + |  | 16 |  | 50 | >100 |
| + | 5 |  | iv | 80 | >100 |
| + | 20 |  |  | 80 | >100 |
| + |  | 4 |  | 80 | >100 |
| + |  | 16 |  | 100 | >100 |
| + | 5 |  | Oral | 70 | >100 |
| + | 20 |  |  | 70 | >100 |
| + |  | 4 |  | 30 | 39 |
| + |  | 16 |  | 20 | 28 |

*Treatment 7 days after sc inoculation of $10^5$ LSTRA cells.
+Treatment 5 days after BCNU therapy.

The increase in MST achieved by BRU-PEL treatment alone in the LSTRA leukemia study (Table 11) prompted us to investigate BRU-PEL as a monotherapy in two other tumor systems, a leukemia (L1210) and a solid tumor (M109). The results in Table 13 show that with decreasing concentrations of L1210 cell inoculum, progressive increases in MST over control values were attained. Although these increases in survival time resulting from BRU-PEL treatment were consistent, they were not considered significant.

TABLE 13

Effect of BRU-PEL monotherapy on L1210 leukemia growth

| BRU-PEL* (mg/kg) | L1210 cell inoculum | | | | |
|---|---|---|---|---|---|
|  | $10^3$ | $10^4$ | $10^5$ | $10^6$ | $10^7$ |
| Placebo | 12+ | 11 | 9 | 8 | 7 |
|  | 11–13++ | 11–13 | 8–10 | 7–9 | 7–7 |
| 8 | 14 | 13 | 10 | 8 | 7 |
|  | 13–15 | 12–13 | 9–10 | 8–9 | 7–7 |
| 16 | 16 | 14 | 11 | 8 | 7 |
|  | 14–19 | 13–15 | 10–12 | 8–9 | 7–7 |

*L1210 tumor cell ip inoculation followed by BRU-PEL ip injection on Day 0 within 3 hrs.
+MST (days) based on 20 animals.
++Range of death (days).

The results of a dose response daily of BRU-PEL in the M109 tumor system indicated that the dose of 100 mg/kg was most effective. The results of monotherapy with BRU-PEL at the 100-mg/kg dose are shown in Table 14. Increases in lifespan were achieved when BRU-PEL was administered by the ip or iv route. All other routes of BRU-PEL treatment were found to be ineffective. The increases in lifespan correlated with the retardation of tumor growth observed in animals treated with BRU-PEL by the ip or iv route (data not shown). It may be that multiple treatments with BRU-PEL may have resulted in more significant effects in both the L1210 and M109 tumor systems; this possibility is presently being investigated. It is interesting to note that the best effects with BRU-PEL were achieved when this agent was administered by the ip or iv route (Tables 11–14).

TABLE 14

Effect of BRU-PEL monotherapy on M109 adenocarcinoma when administered by different routes

| Route of BRU-PEL Injection* | Survival (%) | MST (days) | Increase (%) |
|---|---|---|---|
| Placebo (ip) | 0 | 30 | — |
| Ip | 0 | 40 | 33 |
| Intralesional | 0 | 34 | 13 |
| Contralateral (sc) | 0 | 30 | 0 |
| Iv | 0 | 41 | 36 |
| Intradermal | 0 | 32 | 6 |

*Mice inoculated with $1 \times 10^6$ cells sc and BRU-PEL (100 mg/kg) administered 7 days later when tumors measured 5–8 mm.

Observations from many experiments in our laboratory indicate that the ability of the initial cytoreductive drug regimen to significantly reduce the tumor burden was essential in order for the immunoadjuvant to exert an additive beneficial effect. An evaluation of greater than 40 experiments was made on the tumor-reductive effect of cytoreductive therapy resulting from chemotherapy alone (BCNU, cyclophosphamide, methyl-CCNU, melphalan, or methotrexate), at the maximum tolerated antitumor dose of each drug and compared to the response achieved with the same drug plus adjuvant treatment (levamisole, BRU-PEL, or DIVEMA). The data were divided into two categories: (a) reduction of the local tumor produced by sc inoculation of the LSTRA leukemia from the maximum tumor size of 12 mm to 0–4 or 5–10 mm; and (b) the percent of long-term remissions produced as the result of chemotherapy alone or combined chemotherapy plus adjuvant. The pooled data are presented in Table 15. It became evident that only two drugs, BCNU and methyl-CCNU, were capable of producing a significant number of long-term remissions whether the initial tumor size was reduced to <4 or 10 mm. In comparing the effectiveness of combined chemotherapy and immunoadjuvant, it is clear that in reducing tumor to a nadir of 0–4 mm, the immunoadjuvant provided a beneficial effect which resulted in a significantly higher percentage of long-term remissions. It was also evident that although a reduction of tumor to 5–10 mm occurred by chemotherapy alone, use of immunoadjuvant still produced a higher number of long-term remissions.

Another interesting response noted in this evaluation was that a higher percentage of animals that relapsed died with recurring local subcutaneous tumor and splenomegaly when they received chemotherapy alone, in contrast to animals relapsing that received chemotherapy plus adjuvant.

TABLE 15

Relationship of local tumor burden following chemotherapy and response to immunostimulator

| Drug used for initial cytoreductive therapy of LSTRA leukemia | Long-term remissions (%) Nadir tumor size (mm) | | | |
|---|---|---|---|---|
| | 0–4 | | 5–10 | |
| | Chemotherapy alone | Chemotherapy + IS* | Chemotherapy alone | Chemotherapy + IS* |
| BCNU | 30+ | 70++ | 20 | 40 |
| Cyclophosphamide | 10 | 40 | 10 | 20 |
| Methyl-CCNU | 30 | 70 | 20 | 30 |
| Melphalan | 10 | 40 | 0 | 20 |
| Methotrexate | 0 | 10 | 0 | 0 |

*IS = immunostimulator: levamisole, BRU-PEL, or DIVEMA
+Most of the animals died with evidence of recurrent local tumor and splenomegaly.
++Most of the animals died with splenomegaly.

Results of these tests demonstrate that BRU-PEL, when used together with chemotherapy, exerts a beneficial additive effect resulting in a more prolonged survival and a higher percentage of animals cured of their leukemia. When used as a monotherapy, BRU-PEL exerted a demonstrable, but not significant, effect on the L1210 leukemia. A significant tumor-retarding effect was attained against a slow-growing alveolar carcinoma. A similar response was achieved by BRU-PEL monotherapy of M109 tumor colony formation in the lungs.

The immunoadjuvant activity demonstrated by BRU-PEL was similar to that obtained with levamisole, another reported immunostimulator. A major difference noted for these two agents was that effectiveness was dependent upon the route of administration. The most effective route for BRU-PEL was ip or iv; in contrast, levamisole was active in all routes tested (ip, iv, sc, or oral). BRU-PEL's immunoadjuvant activity was dependent upon the ability of the initial cytoreductive therapy to reduce the tumor burden, although BRU-PEL alone did possess some tumor-retarding effect.

The mechanism through which BRU-PEL may exert its effect was considered to be by stimulation of cells of the reticuloendothelial system. We have recently demonstrated that the ability of adjuvants to enhance host resistance against cancer correlated with the capacity to produce cytotoxic macrophages. In addition, BRU-PEL has demonstrated adjuvant activity when combined with a poorly antigenic tumor. More recently, we have shown that BRU-PEL activates macrophages by a direct mechanism independent of T-lymphocyte factors and independent of any endotoxin contained in the BRU-PEL preparation. The suppression of T and B cells resulting from tumor burden or cytoreductive chemotherapy was apparently reconstituted by the administration of BRU-PEL.

The implication of these observations is that BRU-PEL's immunoadjuvant activity is correlated strongly with its ability to activate, nonspecifically, tumoricidal macrophages and cause reconstitution of the T- and B-cell compartments depressed by cytoreductive therapy.

Additional Macrophage Activation and Antitumor Tests

Comparative tests involving BRU-PEL and *B. abortus lipopolysaccharide* (LPS).

Male BALB/c and CD2F$_1$ mice, 6–8 weeks old, were obtained from the Mammalian Genetics and Animal Production Section, Developmental Therapeutics Program, Division of Cancer Treatment, National Cancer Institute, Bethesda, Md. Homozygous nude mice were supplied by Charles River Breeding Laboratories, Wilmington, Mass. Mice were housed in plastic cages with air-filter bonnets and fed Purina laboratory chow and water ad libitum.

The methods for preparation of BRU-PEL, an aqueous ether extract of a living nonpathogenic strain of *B. abortus*, and *B. abortus* lipopolysaccharide (LPS) have previously been described, FEINGOLD DS, KELETI G. and YOUNGNER JS. Antiviral activity of *Brucella abortus* preparations: separation of active components. Infect Immun 13:763–767, 1976. *Escherichia coli* LPS (0127:B8) and *Salmonella typhimurium* LPS were purchased from Difco Laboratories, Detroit, Mich. All drugs were made up in sterile Dulbecco's phosphate-buffered saline (PBS).

Established cell lines of MBL-2 (H2$^b$[C57BL/6]) murine leukemia and Madison 109 (M109) (H2$^d$[BALB/c]) murine alveolar carcinoma cells were maintained in RPMI-1640 medium supplemented with 20% heat-activated (56° C. for 30 minutes) fetal calf serum (FCS), 100 ug/ml of gentamicin solution, 0.075% NaHCO$_3$, and 10 mM Hepes buffer (RPMI-FCS).

Noninduced peritoneal macrophages were harvested and purified by adherence. Representative preparations of purified adherent cells were stained with Giemsa stain: >95% of the cells observed had morphologic characteristics of macrophages. Macrophages were kept in an ice bath prior to use to prevent adherence.

The ability of activated macrophages to diminish target cell proliferation was measured by the inhibition of DNA synthesis assay previously described. Briefly, target cells were trypsinized from exponentially growing cultures and resuspended at 5.0×10$^4$ cells/ml of RPMI-FCS, and 2-ml aliquots were placed in 30 mm tissue culture dishes. Purified peritoneal macrophages were adjusted to 1.0×10$^6$ cells/ml of RPMI-FCS, and 1 ml was added to the target cell cultures. DNA synthesis of the target cells was assessed after 20 hours of incubation at 37° C. Three cultures of each set of dishes as well as cultures consisting of tumor cells alone and macrophages alone were pulsed with 2.0 microcuries of tritiated thymidine (specific activity, 10 curies/mmol) for 2 hours at 37° C. At the end of the incubation, the cells were detached with trypsin, centrifuged at 600×g for 10 minutes, and resuspended in 0.5 ml of Dulbecco's PBS. Four ml of chilled 10% trichloroacetic acid was added to each tube, and precipitation was allowed to continue for 30 minutes at 4° C. The resultant precipitate was collected on glass-fiber paper and washed with cold 10% TCA. The filters were air-dried and assayed for radioactivity uring Aquasol solubilizer (New England Nuclear Corp., Boston, Mass.). The percent inhibition of DNA synthesis was calculated by the following formula.

$$\% \text{ inhibition of DNA synthesis} = \frac{cpm_N - cpm_E}{cpm_N} \times 100,$$

where $cpm_N$=mean counts per minute in cultures containing effector cells from normal control mice and $cpm_E$=mean counts per minute in cultures containing test effector cells.

In measuring the ability of drugs to produce growth inhibitory macrophages in vitro, approximately 4×10$^5$ peritoneal macrophages contained in 1 ml of RPMI-FCS were seeded in 16 mm wells on Tissue Culture Cluster Plates (Costar, Cambridge, Mass.). After two hours of incubation at 37° C. in a 5% CO$_2$-in-air atmosphere, nonadherent cells were removed by three cycles of aspiration with RPMI-1640 medium. The adherent cells (macrophages) were then overlaid with 4×10$^4$ MBL-2 cells contained in 1.0 ml of RPMI-FCS. Drugs were added in the desired concentrations in an additional 1.0 ml of RPMI-FCS. Toxicity controls consisting of MBL-2 cells alone in the presence of the various drugs were also included in each experiment. Drugs were kept in the culture medium for the duration of the incubation. All cultures were maintained in a humidified, 5% CO$_2$-in-air incubator at 37° C., and viable leukemia cells were counted daily with a hemocytometer. Percent growth inhibition of MBL-2 cells due to macrophage-drug interaction was calculated by comparison to MBL-2 cells grown in the presence of normal macrophages alone.

With regard to inhibition of artificially induced lung metastases, M109 cells grown in vitro were harvested during their exponential growth phase by gentle trypsinization, were washed twice, and were resuspended in serum-free RPMI-1640. The number of single viable cells was determined and adjusted to 1×10$^5$ cells/ml of medium. Tumor cells were injected iv in normal BALB/c mice. Inoculum volume per mouse was 0.2 ml (2×10$^4$ cells). Drugs were given ip to randomized groups of mice 5 days prior to tumor cell inoculation. Controls received 0.2 ml of Dulbecco's PBS. Five mice from each group were killed on Days 14 and 20, and the number of pulmonary metastases was determined by India ink inflation by the technique of Wexler.

BRU-PEL was compared to various LPS preparations for the ability to transform normal resting macrophages into cytotoxic effector cells in vitro (Table 16). BRU-PEL activated macrophages to inhibit MBL-2 leukemia cell growth with optimal activity at 10 ug/ml, although significant activity remained at concentrations as low as 1 ng/ml. LPS preparations derived from *E. coli* and *S. typhimurium* showed kinetics similar to those of BRU-PEL. In contrast, LPS from *B. abortus* did not have any effect on resting macrophages at any of the concentrations tested. None of these preparations had a direct inhibitory effect on MBL-2 target cells in the absence of macrophages.

TABLE 16

| | Ability of bacterial agents to activate murine peritoneal macrophages in vitro | | | | | |
|---|---|---|---|---|---|---|
| | Growth inhibition* at 48 hrs of-- | | | | | |
| Bacterial agent | 100 ug/ml | 10 ug/ml | 1 ug/ml | 100 ng/ml | 10 ng/ml | 1 ng/ml |
| BRU-PEL | ++ | ++ | ++ | + | + | + |
| B. abortus | NT+ | − | − | − | − | − |
| E. coli LPS | ++ | ++ | ++ | ++ | + | − |
| S. typhimurium LPS | ++ | ++ | ++ | + | − | − |

*− = Growth inhibition of MBL-2 target cells <25%; + = between 25% and 50%; ++ = >50% of control value.
+NT = not tested.

The effect of ip BRU-PEL treatment on macrophage reactivity from BALB/c and athymic nude (nu/nu) mice was studied. Macrophages from both strains of mice potently arrested DNA synthesis of M109 lung carcinoma cells when harvested 6 days after BRU-PEL treatment Macrophage activation by BRU-PEL was thymus-independent and was not dose-dependent over a range of 1–100 mg/kg.

The effect of BRU-PEL on artificially induced pulmonary metastases was considered.

Pyran copolymer (NSC-46015) has previously been shown to retard the development of experimental M109 lung metastases. To determine whether BRU-PEL was similarly effective in potentiating surveillance against M109 pulmonary metastases, BRU-PEL or 0.9% NaCl solution was administered ip 5 days prior to iv tumor inoculation. Mice were killed on Days 14 and 20, and their lungs were inflated with India ink in order to visualize tumor nodules. BRU-PEL strikingly reduced the number of pulmonary lesions in two separate experiments (Table 17). In contrast to multiple tumors in the lungs of placebo-treated mice, a few lungs (four of ten) from BRU-PEL-treated mice remained tumor-free on Day 20. B. abortus LPS was without effect on experimental metastases development.

TABLE 17

Inhibition of artificially induced lung metastases of M109 lung carcinoma by BRU-PEL

| Drug treatment* | Mean No. of lesions ± SE/lung+ (Day 14) | No. of mice with lung tumors/ total No. of mice | Mean No. of lesions ± SE/lung+ (Day 20) | No. of mice with lung tumors/total No. of mice |
|---|---|---|---|---|
| Experiment 1 | | | | |
| Control | 4.0 ± 0.4 | 5/5 | 117.0 ± 54.3 | 5/5 |
| BRU-PEL (Day - 5) | 0.0 ± 0.0 | 0/5 | 2.8 ± 0.9 | 4/5 |
| Experiment 2 | | | | |
| Control | 9.4 ± 1.8 | 5/5 | >250 | 5/5 |
| BRU-PEL (Day - 5) | 0.2 ± 0.2 | 1/5 | 0.6 ± 0.4 | 2/5 |
| B. abortus LPS (Days - 5) | 5.0 ± 2.0 | 4/5 | >250 | 5/5 |

*BRU-PEL and B. abortus LPS were administered ip at 100 and 2 mg/kg respectively.
+2 × $10^4$ M109 cells were injected iv on Day 0. Lung lesions were identified by inflation with India ink.

These tests show that BRU-PEL activated macrophages by a direct mechanism independent of T-lymphocyte factors. In this regard, BRU-PEL was similar to a number of polyanions in its kinetics of macrophage activation in vitro and may result from an interferon induction mechanism. Although BRU-PEL contains endotoxin (as measured by the Limulus amebocyte assay), we show that LPS derived from B. abortus lacked effect on macrophage functional activity. Although it is known that lipid A of gram-negative bacterial endotoxin activates macrophages, it appears that the lipid A of enterobacteria is different from Brucella. This might explain the inability of B. abortus LPS to activate macrophages in vitro.

Pretreatment of mice with BRU-PEL, but not B. abortus LPS, potently inhibited lung metastasis formation. Preliminary histopathologic observations of the host response to tumor give further support to the role of the activated macrophage in tumor surveillance. Macrophage accumulations in the interstitium of the lungs from BRU-PEL-treated animals were observed to encircle the metastatic foci and completely arrest their development. Our current data support the concept that activated macrophages have a surveillance function in inhibiting or controlling metastatic cell growth. Moreover, the enhancement of macrophage numbers and activity in the lungs following systemic BRU-PEL treatment could provide an approach to possible treatment.

The BRU-PEL substance could conceivably be used to increase a patient's immunological defenses in cancer therapy. Surgical resection, chemotherapy and radiotherapy are indispensable weapons in fighting cancer. However, these agents are often not successful in eliminating the "last cancer cell", and the malignancy is not eradicated. Eradication of the last cancer cell might be accomplished with active participation of the patient's own immune cellular defenses. The availability of an effective, nontoxic material capable of stimulating a patient's immune defenses would represent a significant advance in the treatment of human malignancy.

It will be appreciated therefore that the present invention provides a process for inhibiting tumor development either prior to formation or within a reasonable time thereafter. Tests upon animals have confirmed the superiority of BRU-PEL to two conventional antitumor devices, i.e. BCG and C. parvum. The successful use of BRU-PEL as an inhibiting agent for resisting tumor development in animals indicates that BRU-PEL is a likely candidate for use in humans as an antitumor agent.

While in the foregoing description, a particular strain of Brucella abortus, i.e. strain 456, has been employed in the experiments, as it is a safe strain with respect to potential hazards to humans exposed to the same, it will be appreciated that other strains of Brucella abortus* may be employed in the preparation of BRU-PEL. Also, while a specific method of extraction with aqueous ether has been described, other methods of extraction of BRU-PEL might be employed.

Whereas, particular embodiments of the invention have been described above for purposes of illustration, it will be evident to those skilled in the art that numerous variations of the details may be made without departing from the invention as defined in the appended claims.

We claim:

1. A process of inhibiting tumors in a patient comprising providing BRU-PEL in a dosage effective to resist tumor development in said patient, and administering said BRU-PEL to said patient.

2. The process of claim 1 including administering said BRU-PEL by injection.

3. The process of claim 1 including administering said BRU-PEL into said patient prior to the appearance of visible tumors.

4. The process of claim 1 including administering said BRU-PEL into said patient intraperitoneally.

5. The process of claim 1 including administering said BRU-PEL into mice intraperitoneally in dosages of about 100 micrograms to about 2,000 micrograms.

6. The process of claim 1 including administering said BRU-PEL into said patient asynchronously with at least one other antitumor agent administered in a dosage less than the maximum tolerated antitumor dose of said other antitumor agent.

7. The process of claim 6 including employing at least one member of the group consisting of cyclophosphamide, methyl-CCNU, melphalan, methotrexate and BCNU as a said other agent.

8. The process of claim 1 including providing said BRU-PEL by aqueous ether extraction from *Brucella abortus*.

9. The process of claim 1 including employing said process to inhibit tumors selected from the group consisting of carcinomatous tumors and sarcomatous tumors.

10. The process of claim 1 including employing said process to inhibit Sarcoma-180 ascites tumors.

11. The process of claim 1 including employing said process to inhibit one or more tumors selected from the group consisting of osteogenic sarcoma, L1210 leukemia LSTRA leukemia, alveolar carcinoma, lymphocytic leukemia, Madison 109 lung carcinoma and mammary carcinoma.

* * * * *

UNITED STATES PATENT AND TRADEMARK OFFICE
CERTIFICATE OF CORRECTION

PATENT NO. : 4,842,855

DATED : June 27, 1989

INVENTOR(S) : JULIUS S. YOUNGNER et al.

It is certified that error appears in the above-identified patent and that said Letters Patent is hereby corrected as shown below:

Columns 4 and 5, in TABLE 2, in the heading of the first column, "Tme" should be --Time--.

Column 6, TABLE 4, the second entry in the first column should read --BRU-PEL (1,000 ug in 0.2 ml, ip)--.

Column 6, TABLE 4, in the third entry in the first column, a beginning parenthesis --(-- should be inserted before "1,000".

Column 13, line 51, "demostration" should be --demonstration--.

Column 16, line 26, in the last column of TABLE 12, "<100" should be -- >100--.

Column 21, TABLE 17, in the last entry in the first column "(Days - 5)" should be --(Day - 5)--.

Signed and Sealed this

Third Day of April, 1990

*Attest:*

HARRY F. MANBECK, JR.

*Attesting Officer*       *Commissioner of Patents and Trademarks*